United States Patent
Garcia Lopez et al.

(10) Patent No.: US 6,635,458 B2
(45) Date of Patent: Oct. 21, 2003

(54) ENZYMATIC PROCESS FOR THE PREPARATION OF CEPHALOSPORANIC 7$B(G)-(4-CARBOXYBUTANAMIDE) ACID BY MEANS OF THE MODIFIED ENZYME D-AMINOACID OXIDASE OF TRIGONOPSIS VARIABILIS PRODUCED IN ESCHERICHIA COLI

(75) Inventors: Jose Luis Garcia Lopez, Madrid (ES); Estrella Cortes Rubio, Madrid (ES); Jorge Alonso Palacios, Madrid (ES); Encarnacion Mellado Duran, Leon (ES); Bruno Diez Garcia, Leon (ES); Jose Manuel Guisan Seijas, Madrid (ES); Franciso Salto Maldonado, Madrid (ES); Barredo Fuente, Leon (ES)

(73) Assignee: Antibioticos, S.A.U., Leon (ES)

( * ) Notice: Subject to any disclaimer, the term of this patent is extended or adjusted under 35 U.S.C. 154(b) by 0 days.

(21) Appl. No.: 09/308,683

(22) PCT Filed: Sep. 24, 1998

(86) PCT No.: PCT/ES98/00262
§ 371 (c)(1),
(2), (4) Date: Jul. 15, 1999

(87) PCT Pub. No.: WO99/15632
PCT Pub. Date: Apr. 1, 1999

(65) Prior Publication Data
US 2003/0119087 A1 Jun. 26, 2003

(30) Foreign Application Priority Data
Sep. 25, 1997 (ES) ................................ 9702008

(51) Int. Cl.[7] ............................ C12N 9/04; C12N 1/20; C12N 15/00; C12N 5/00; C07K 1/00
(52) U.S. Cl. .................... 435/190; 530/350; 435/320.1; 435/252.3; 435/325
(58) Field of Search .............................. 435/190, 320.1, 435/325, 252.3; 530/350

(56) References Cited

U.S. PATENT DOCUMENTS

| | | | |
|---|---|---|---|
| 3,941,657 A | 3/1976 | Mazarguil et al. | 195/66 R |
| 5,284,933 A | 2/1994 | Dobeli et al. | 530/350 |

OTHER PUBLICATIONS

Rowland et al., EMBO J., 14(1), 196–205, 1995.*
Peters et al., Eur. J. Biochem., 228, 798–804, 1995.*
Dent et al., Biochem. J., 303(1), 105–112, 1994.*
Annunen et al., J.B.C., 272(28), 17342–17348, 1997.*
Wollscheid et al., Protein Expression and Purification, 11, 241–249, 1997.*
Schrader and Andreeses Jr. (1993) Evidence of the functional important of Cys298 in D–amino acid oxidase from *Trigonopsis viriabilis, Eur. J. Biochem.*, 218:735–744.
Schrader and Andreesen Jr. (1996) Studies of the inactivation of the flavoprotein D–amino acid oxidase from *Trigonopsis viriabilis, Appl. Microbiol. Biotechnol* 45:458–464.
Alonso et al. (1999) Engineering of the D–amino acid oxidase from *Trigonopsis viriabilis* to facilitate its overproduction in *E. coli* and its downstream processing by tailor-made metal chelate supports, *Enzyme and Microbial Technology* 25:88–95.
Derwent Publication AN–87–359677/51 abstract if JP62262994.
Deshpande et al. (1987) Biotechnology Techniques 1:55–58.
Hochuli (1988) J. Chromatoraphy 444:293–302.
Kim et al. (1995) Biotechnology Techniques 9:863–868.
Kubicek–Pranz et al. (1985) J. Applied Biochemistry 7:104–113.
Pollegioni et al. (1993) Biochemistry and Molecular Biology Internatonal 31: 709–717.
Porath et al. (1983) Biochemistry 22: 1621–1630.

* cited by examiner

Primary Examiner—Maryam Monshipouri
(74) Attorney, Agent, or Firm—Baker Botts LLP

(57) ABSTRACT

Enzymatic process for the preparation of cephalosporanic 7β-(4-carboxybutanamide) acid by using the modified enzyme D-aminoacid oxidase of *Trigonopsis variabilis* produced in *Escherichia coli*. The process for the expression of the enzyme comprises: (I) isolating the DNA corresponding to gene which codes for the enzyme D-aminoacid oxidase; (II) removing the intron which is contained in said gene; (III) inserting the DNA fragment obtained into the plasmide which is capable of replication in *Escherichia coli;* (IV) fusing at the extremity 5' of the structural region of the gene a synthetic assembler which contains a nucleotide sequence which codes for six histidines; (V) transforming a strain of *Escherichia coli* with the resulting recombinant plasmide; (VI) cultivating the transformed cells of *Escherichia coli;* and (VII) recovering the enzyme D-aminoacid oxidase of the former cultivation operation through affinity chromatography.

6 Claims, 1 Drawing Sheet

Figure 1:
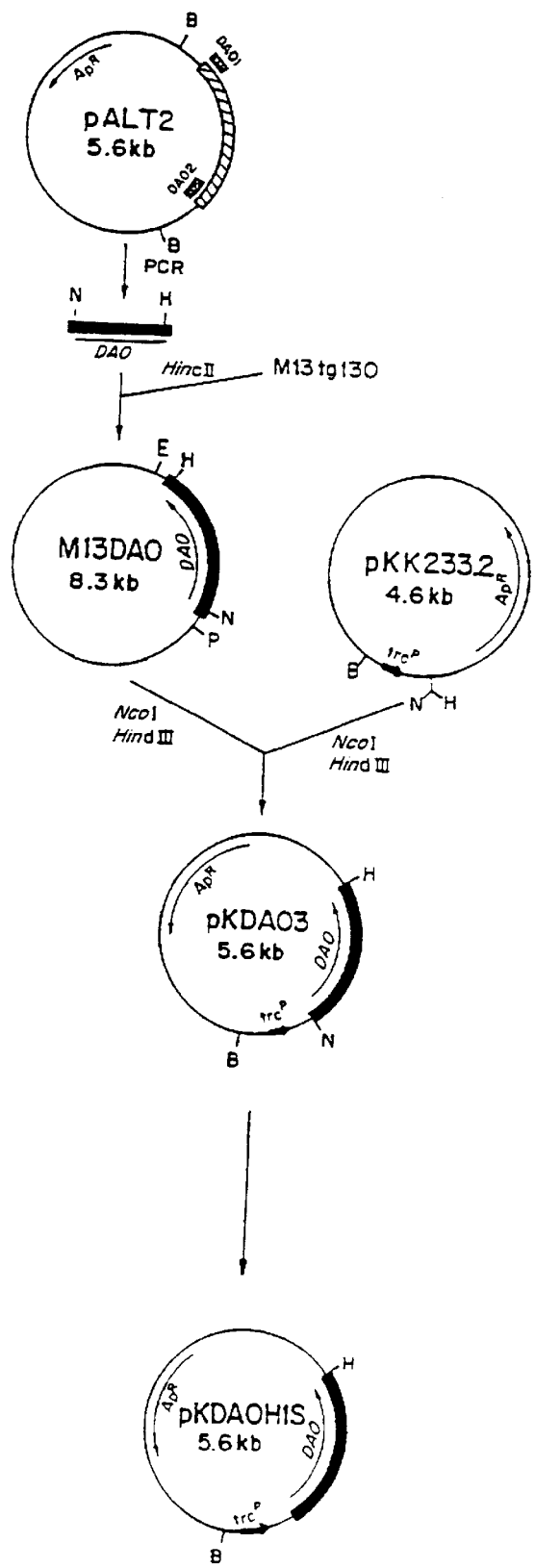

ENZYMATIC PROCESS FOR THE PREPARATION OF CEPHALOSPORANIC 7$B(G)-(4-CARBOXYBUTANAMIDE) ACID BY MEANS OF THE MODIFIED ENZYME D-AMINOACID OXIDASE OF TRIGONOPSIS VARIABILIS PRODUCED IN ESCHERICHIA COLI

FIELD OF THE INVENTION

The present invention relates to an enzymatic process for the preparation of 7β-(4-carboxybutanamide) cephalosporanic acid. More particularly, it describes a method for isolating the gene which codes for an enzyme with D-aminoacid oxidase activity by the use of recombinant DNA techniques, the cloning of said gene in a microorganism of the genus Escherichia, the modification of said enzyme by protein engineering techniques, the hyperproduction of said modified enzyme by fermentation in said microorganism and the extraction of the modified enzyme for preparation of 7β-(4-carboxybutanamide) cephalosporanic acid. This acid is an intermediate compound for the preparation of 7-amino cephalosporanic acid, which in turn is a known intermediate for the preparation of a wide variety of antibacterial agents in the cephalosporins family.

PRIOR ART

For the production of 7β-(4-carboxybutanamide) cephalosporanic acid, also called glutaryl-7-aminocephalosporanic acid (hereinafter referred to as GL-7ACA), from cephalosporin C, the use of the enzyme D-aminoacid oxidase (hereinafter referred to as DAO) from various microorganisms such as *Trigonopsis variabilis* (Biochem. Biophys. Res. Commun. (1993) 31: 709), *Rhodotorula gracilis* (J. Biol. Chem. (1994) 269: 179) and *Fusarium solani* (J. Biochem. (1990) 108: 1063) is known. The production of DAO by the use of these microorganisms involves many disadvantages. For one thing, the level of production of DAO activity is very low, and, for another, other undesirable enzyme activities such as esterases and catalases are present together with said enzyme. The former break down GL-7ACA acid, reducing the yield and thus increasing the costs of the purification process. The latter destroy the hydrogen peroxide needed in the catalysis and necessitate the addition of this compound, which also increases the costs of the process and at the same time causes a loss in the activity of the enzyme, reducing its possibilities of re-use. In order to avoid said enzymatic contamination it is necessary to purify the DAO activity, which greatly increases the costs and difficulty of the enzymatic process for obtaining GL-7ACA from cephalosporin C.

A process has recently been described for isolating the gene which codes for DAO in *T. variabilis* and expressing it in *E. coli* and in *T. variabilis* (Japanese Patent Application Laid-Open No. 71180/1988; European Patent Application No. 93202219.7, Publication No. 0583817A2). Moreover, the gene which codes for the DAO activity of *F. solani* has also been cloned and expressed in *E. coli* and *Achremonium chrysogenum* (Japanese Patent Application Laid-Open No. 2000181/1990; J. Biochem. (1990) 108: 1063; Bio/Technology (1991) 9: 188) and more recently the gene which codes for DAO in *R. gracilis* has been cloned and expressed in *E. coli* (Spanish Patent P9600906).

In view of the great interest that the availability of a purified DAO activity has industrially for the production of GL-7ACA, the objective of the present invention was centred on the production of an enzyme with DAO activity which could easily be purified. In this sense it is known that one of the most effective ways of purifying a protein is the use of affinity chromatography (Sassenfeld, H. M. (1990) Trends Biotechnol. 8: 88). For this purpose it is necessary to find a chromatographic support which allows the selective binding and/or elution of the protein of interest. Said chromatographic support must contain a recognition molecule or ligand for said protein in such a way that the interaction between it and the ligand is specific and strong enough to allow the selective elution of the protein. The development of an affinity chromatography support is not simple, and until now no process allowing the affinity purification of DAO enzyme activities in a single step has been described.

Furthermore it is known that certain genetic engineering processes allow the modification of proteins, improving particular properties which facilitate the purification thereof. Thus, various systems have been developed for modification of the structure of a protein to allow its affinity purification (Sii, D. and Sadana, A. (1991) J. Biotechnol. 19: 83; Narayanan, S. R. and Crane, L. J. (1990) Trends Biotechnol. 8: 12; Scouten, W. H. (1991) Curr. Opinion Biotechnol. 2: 37; Sassenfeld, H. M. (1990) Trends Biotechnol. 8: 88). In essence these modifications consist in fusing to the protein a polypeptide which has specific properties of interaction with a particular chromatographic support and which therefore gives the fusion protein the ability to be purified by affinity chromatography. One of these modifications consists in fusing to the protein in question a polyhistidine sequence which gives the fusion protein the ability to be purified by affinity chromatography using a support which contains divalent metal ions (Arnols, F. H. (1991) Bio/Technology 9: 151; Hochuli et al. (1988) Bio/Technology 6: 1321).

Although the obtaining of fusion proteins to improve the purification properties is in principle a simple and effective technique, its major disadvantage resides in the fact that the modification of a protein in its primary structure involves changes which may have an important effect on its secondary, tertiary and quaternary structure. These changes in structure may affect the protein to such an extent that it entirely or partially loses its functionality, converting it into a protein which is useless for the function that had been envisaged. The obtaining of a fusion protein therefore always entails great uncertainty, as the final result is largely unpredictable, especially when the first fusion experiment is being carried out, i.e. when the result of previous fusions is not known. It is in this uncertainty of the final result that the novelty of the process for obtaining a fusion protein lies, as it is not possible at present to predict with certainty what will happen when a protein fusion experiment is carried out.

In the scientific literature there is no description of any process for producing the DAO enzyme of *T. variabilis* genetically modified in such a way as to allow its purification in a single step and that it can be hyperproduced in an active form either in *E. coli* or in another microorganism.

DETAILED DESCRIPTION OF THE INVENTION

For the description of this invention the starting point is the yeast *T. variabilis* ATCC 20931 as donor of deoxyribonucleic acid (hereinafter referred to as DNA). Once the genomic DNA of the yeast (which contains the gene with the genetic information relating to the production of DAO, hereinafter also called dao gene) had been obtained, it was used to construct a DNA library in *E. coli* using the phage vector λ-GEM12. The analysis of the DNA library was performed by standard hybridization techniques using as probes synthetic oligonucleotides designed on the basis of regions of similarity found between different DAOs. In this way a series of recombinant clones of E. coli were isolated which contained a T. variabilis DNA fragment coding for the dao gene. The DNA fragment so obtained was subcloned in a plasmid vector obtained from a strain of E. coli. The recombinant vector was used to obtain the sequence of the DNA fragment which contained the dao gene of T. variabilis (SEQ ID NO: 1). Analysis of said sequence allowed characterization of the dao gene, which is structured in two exons and one intron.

As the DNA fragment previously obtained which contains the genomic sequence of the dao gene of T. variabilis has one intron, it cannot be used directly for its expression in E. coli. Steps were therefore taken to obtain a dao gene lacking said intron. For this purpose the dao gene was amplified by PCR using two synthetic oligonucleotides. The first of these was designed in such a way as to contain the following elements: a ribosome binding site, a translation initiation site, the complete sequence of the first exon and the first nucleotides of the 5' end of the second exon. The second oligonucleotide contained the complementary sequence of the 3' end corresponding to the second exon of the dao gene, including a translation termination codon. Different restriction sites useful for the cloning of DNA fragments were also included in these synthetic oligonucleotides. In this way a new DNA fragment was obtained which, after being isolated, was cloned in an E. coli plasmid vector (FIG. 1). Using the previously created restriction targets, the DNA fragment which contained the complete dao gene without the intron was subsequently subcloned in different E. coli plasmid vectors which had promoters that allowed the overexpression of genes in this host bacterium. The DAO activity produced by the various clones was assayed by colorimetric techniques and by HPLC chromatography. In this way recombinant clones of E. coli were obtained which produced a large amount of active DAO enzyme.

The dao gene was then modified by adding a nucleotide sequence coding for a polyhistidine. For this purpose a plasmid containing the dao gene was digested with a restriction enzyme which cut in the translation initiation codon, and the DNA ends resulting from the digestion were blunted with the Klenow fragment of the DNA polymerase I of E. coli. They were then ligated in the presence of a synthetic linker which contained the codons of the polyhistidine, with which a plasmid was produced that contained the modified dao gene in the 5' end of its coding region (SEQ ID NO: 2). The recombinant plasmid so produced was transformed in a strain of E. coli and selected by hybridization techniques using the oligonucleotides of the polyhistidine linker as probes. The modified dao gene was sequenced in order to check that the desired fusion had been correctly produced.

The production of DAO modified with polyhistidine (hereinafter called hisDAO) was then studied, using various strains of E. coli as hosts of the previously constructed plasmids. In this way it was checked that the enzyme hisDAO was active.

For the production of hisDAO using the previously selected recombinant clones of E. coli, they are cultured in a medium containing a carbon source, a nitrogen source and mineral salts. The incubation temperature is between 18° C. and 37° C. and the pH must be maintained between 5 and 9. Flasks of various volumes, from 50 ml to 1000 ml, can be used for small-scale fermentation, with a quantity of medium between 10% and 50% of the volume of the flask. The duration of the fermentation can range from 12 to 90 hours.

The production of DAO by the recombinant microorganism can be improved if cultural conditions suitable for maintaining the stability of the recombinant vectors are chosen, which is achieved by adding to the culture medium the antibiotics for which the recombinant vector containing the dao gene shows a resistance marker (ampicillin, chloramphenicol, kanamycin, tetracycline, etc.). Apart from stabilizing the production, this prevents contamination of the culture medium by other undesirable microorganisms and also eliminates the strains which, because they have lost the recombinant vector, have stopped producing DAO.

The recombinant hisDAO-producing cells were separated from the culture medium by centrifugation and were then disrupted or permeabilized by means of chemical, enzymatic or mechanical processes. In order to obtain an enzymatic extract of greater purity the hisDAO was purified in a single step by affinity chromatography in columns of $Co^{2+}$-IDA. For this purpose the crude enzymatic extract was loaded in a $Co^{2+}$-IDA resin and the contaminant proteins were eluted by a washing with 20 mM phosphate buffer, pH 7.0, containing 0.2 M NaCl. The hisDAO enzyme was then eluted by a washing with 10 mM imidazole.

If $Cu^{2+}$-IDA or $Zn^{2+}$-IDA is used as the chromatographic support instead of Co2+-IDA, the hisDAO enzyme remains strongly bound to the matrix in active form without it being possible to elute it with high concentrations of imidazole. In this way the support, suitably washed to eliminate the contaminant proteins, can be used as an immobilized enzyme system.

Using the hisDAO enzyme purified from the recombinant clones of E. coli that expressed the chimeric gene, GL-7ACA was obtained from cephalosporin C.

The dialysed and concentrated enzymatic extracts obtained from the chromatography on the $Co^{2+}$-IDA support can also be immobilized by making them react with other suitable inert solid supports, with the possibility of using immobilized hisDAO cyclically.

The novelty of this invention resides in the fact that this is the first time that the enzyme DAO of the yeast T. variabilis, modified as hisDAO, can be expressed in an active form in a prokaryotic microorganism such as E. coli and purified in a single step by affinity chromatography. In addition, an increase in the production of DAO relative to the quantity obtained in T. variabilis has been achieved, which facilitates the use of this enzyme on an industrial scale. The possibility of producing hisDAO in different strains of E. coli which do not have undesirable enzymes such as catalase or esterases, and also the possibility of improving the stability and catalytic properties thereof by means of further modifications by protein engineering techniques, are other aspects which increase the novelty concept of this patent.

The present invention, without any limitation, will be illustrated in greater detail in the Examples that are described below.

EXAMPLE 1

1.—DAO Activity Assay

The DAO activity assay was performed by a procedure described previously (J. Biol. Chem. (1967) 242: 3957), using D-phenylglycine (25 mM) as substrate. The incubation was carried out in 50 mM phosphate buffer, pH 8.0, for 15 to 30 minutes, the reaction being stopped with ⅒ the volume of pure acetic acid. The variation in the OD at 252 nm determines the activity of the enzyme, taking into account that 89.77 nmol of the benzoylformic acid which is produced in the reaction shows an $OD_{252}$ of 1.0.

2.—Preparation of the DNA Vectors and of the Competent E. coli Cells for the Transformation The plasmid vectors pBluescript I KS (+) (Ap$^r$) (Stratagene) and pKK233.2 (Ap$^r$) (Pharmacia) were prepared by the alkaline lysis method (Sambrook et al. (1989) Molecular Cloning: A Laboratory Manual, Cold Spring Harbor Laboratory, Cold Spring Harbor, N.Y., USA). For this purpose the E. coli strains carrying the aforesaid plasmids were incubated for 16 hours with agitation in an orbital shaker at 250 rpm and 37° C. in 500 ml of LB with 100 µg/ml of ampicillin. The plasmid DNA obtained by this method was purified by centrifugation in CsCl gradient.

The competent cells of E. coli TG1 and E. Coli DH5α were obtained by the RbCl procedure (Sambrook et al. (1989) Molecular Cloning: A Laboratory Manual, Cold Spring Harbor Laboratory, Cola Spring Harbor, N.Y., USA).

3.—Preparation of the Donor DNA Which has the Genetic Information Relating to the Production of DAO The strain T. variabilis ATCC 20931 was cultured in YMPG medium (malt extract 0.3%, yeast extract 0.3%, peptone 0.5% and glucose 1%). Incubation was continued for 36 hours ($OD_{660}$=5.0), with agitation in an orbital shaker at 250 rpm and at a temperature of 30° C.

The cells were then sedimented, washed and lysed with zymolyase, and the DNA was extracted by a previously described procedure (Sherman et al. (1986) Laboratory Course for Methods in Yeast Genetics, Cold Spring Harbor Laboratory, Cold Spring Harbor, N.Y.). In order to achieve greater purity the DNA was treated with RNase, extracted several times with phenol and chloroform-isoamyl alcohol 24/1 (CIA) and precipitated with isopropanol. The DNA precipitated was washed with 100% ethanol and 70% ethanol and dissolved in the 10 mM Tris-HCl buffer, pH 7.5, containing 1 mM EDTA (TE buffer).

EXAMPLE 2

1.—Construction of a T. variabilis DNA Library

The total DNA of the strain T. variabilis ATCC 20931 was obtained as described in Section 3 of Example 1. A total of 300 µg of said total DNA was partially digested with 20 units of Sau3AI in a reaction volume of 600 µl at 37° C., and 3 aliquots of 200 µl were collected at 45 seconds, 1 minute and 2 minutes, respectively, the digestion being stopped with cold 20 mM EDTA. After checking the digests in a 0.7% agarose gel, they were mixed, heated to 68° C. for 10 minutes, left to cool slowly to ambient temperature and placed on a 38 ml (10–40%) sucrose gradient. Said gradient was centrifuged at 26,000 rpm for 24 hours at 15° C., aliquots of 0.5 ml being collected, 10 µl of which was analysed in an 0.4% agarose gel. The aliquots whose DNA had a size between 18 and 22 kb were mixed and diluted with distilled water to approximately 10% sucrose. The DNA was then precipitated with ethanol and resuspended in 50 µl of a TE buffer, and 3 µl of the latter solution was analysed in an 0.4% agarose gel. In said gel it was checked that the size of the DNA fragments was correct and that their concentration was approximately 50 ng/µl.

In parallel the DNA of the bacteriophage λ-GEM12 (Promega) was prepared by previously described procedures, with slight modifications (Sambrook et al. (1989) Molecular Cloning: A Laboratory Manual, Cold Spring Harbor Laboratory, Cold Spring Harbor, N.Y., USA). For this purpose the strain E. coli NM538 (Promega) was grown for 10 hours in NZCYM-0.2% maltose and its OD was measured at 600 nm. The volume of culture corresponding to $3 \times 10^9$ cells was centrifuged at 4000 rpm for 10 minutes at 4° C. in a bench centrifuge and resuspended in 1.2 ml of SM buffer. To these cells $3 \times 10^7$ plaque-forming units (pfu) of the phage λ-GEM12 were added and the mixture was incubated for 30 minutes at 37° C. without agitation. Each of the flasks (of 500 ml, with 100 ml of NZCYM-0.2% maltose medium) preheated to 37° C. was inoculated with 200 µl of the infected cells. Said flasks were incubated at 37° C. until the culture appeared lysed (5–6 hours). The lysates were treated with DNase (1 µg/ml) and RNase (2 µg/ml) for 45 minutes at ambient temperature. Next, 5.8 grams of NaCl was added per 100 ml of lysate, and the mixture was kept for 60 minutes in ice. After this time had elapsed the lysate was filtered to eliminate the cellular residues, and after adding 20 ml of 50% PEG-6000 per 100 ml of lysate the mixture was kept for 60 minutes in ice and centrifuged at 10,000×g for 20 minutes at 4° C. The precipitate was resuspended in 1 ml of TE buffer and extracted twice with CIA to eliminate the remnants of PEG-6000 without disrupting the phage. It was then extracted twice with neutral phenol, once with phenol-CIA and once with CIA. The aqueous phase was brought to 0.5 M NaCl (with 4 M NaCl) and the DNA was precipitated with two volumes of ethanol at −20° C. After centrifuging for 20 minutes at 4° C. and 12,000 rpm in a minicentrifuge, the precipitated DNA was washed with 70% ethanol, dried and resuspended in 50 µl of TE buffer.

50 Rg of DNA from the bacteriophage was digested with the endonucleases BamHI and XbaI at 37° C. for 2 hours. The double digest was extracted with phenol-CIA and CIA, precipitated with ethanol and resuspended in 50 µl of TE buffer. After collecting an aliquot of 2 µl, $MgCl_2$ was added to the remainder up to 10 mM and it was incubated for 1 hour at 42° C. in order to encourage the recircularization of the arms of the vector by its cohesive ends. A 2-µl fraction which was analysed together with the previous one in an 0.5% agarose gel was again collected. After correct recircularization by the cohesive ends had been verified, the mixture was placed on a 38-ml sucrose gradient (10–40%). In this case the DNA was not heated at 68° C. before it was placed on the gradient, as this would lead to separation of the cohesive ends of the phage. The gradient was centrifuged at 26,000 rpm for 24 hours at 15° C., subsequently being collected in aliquots of 0.5 ml. After analysing 15 µl of each of these in an 0.5% agarose gel, those which lacked the dispensable central fragment or "stuffer" were mixed and diluted with distilled water up to about 10% sucrose. The DNA was precipitated with ethanol and resuspended in 50 µl of TE, and 2 µl of the latter solution was visualized in an agarose gel (0.5%) in order to confirm the absence of the central fragment and estimate that its approximate concentration was 100 ng/µl.

A series of ligations were then performed, using 0.25 µg of insert and quantities of vector ranging from 0.25 to 0.75 µg, varying the insert/vector ratio. The reactions were incubated at 12–14° C. for 16 hours. After verifying, in an 0.4% agarose gel, that DNA fragments (produced by ligation) of greater size than that of the vector or insert had appeared, all the ligation reactions were mixed, precipitated with ethanol and resuspended in 4 µl of ligation buffer.

The packaging of the recombinant phage DNA produced after the ligation was carried out with Packagene (Promega) "in vitro" packaging extracts. The result of the packaging reaction, resuspended in 500 µl of SM, was used to make infections of E. coli NM538, in order to titrate the number of phages present, and of E. coli NM539 (Promega), with the aim of determining the percentage of recombinant phages. E. coli NM539 is a lysogenic strain of the phage P2 and only produces lysis plaques when the phage which infects it lacks the dispensable central region. The DNA library constructed contained some 200,000 pfu and about 85% of the phages carried an exogenous DNA fragment.

After these calculations had been carried out, *E. coli* NM539 was infected and the complete genetic library was spread on Petri dishes of 150 mm diameter.

2.—Identification of the Clones Which Contain the dao Gene

The complete DNA library was transferred to nitrocellulose filters and the process of selecting positive phages was carried out in accordance with a previously described hybridization procedure (Sambrook et al. (1989) Molecular Cloning: A Laboratory Manual, Cold Spring Harbor Laboratory, Cold Spring Harbor, N.Y., USA). The process commenced with the prehybridization of the nitrocellulose filters by incubating them at 42° C. for 3 hours in hybridization buffer. The hybridization was carried out by removing the buffer used in the pre-hybridization and introducing a new hybridization buffer together with 10 pmol of the oligonucleotides OA (5'-TCTTGTCCTCGACACC-3') (SEQ ID NO:3) and OB (5'-GACGTGGATTGTCAACTG-3') (SEQ ID NO:4) labelled at their 5' end with $^{32}$P by means of polynucleotide kinase of the phage T4 and [γ-$^{32}$P] ATP (ICN Biochemicals) by standard procedures (Sambrook et al. (1989) Molecular Cloning: A Laboratory Manual, Cold Spring Harbor Laboratory, Cold Spring Harbor, N.Y., USA). The filters were incubated at 42° C. for 16 hours and washed twice for 20 minutes at ambient temperature in 2×SSC-0.1% SDS, followed by a further two washings for the same length of time at the hybridization temperature in 0.1×SSC-0.1% SDS buffer. Finally, the nitrocellulose filters were exposed with Hyperfilm-MP (Amersham) under amplification screens at −70° C. for 48 hours.

Once the process of pre-hybridization, hybridization, washings and autoradiography was completed, 63 clones which produced positive signals with the two probes OA and OB were selected. Only 9 of the positive lysis plaques were collected individually with the aid of a Pasteur pipette and each of them was resuspended in 1 ml of SM plus 50 μl of chloroform. The phages present in this solution were then titrated. For this purpose it was necessary to dilute said phage 5000 times in order to ensure that when infection was carried out with 20 μl of it, the number of lysis plaques per Petri dish would be between 500 and 1000. Once the contents of each Petri dish had been transferred to the corresponding nitrocellulose filter, the latter were hybridized again with the same probes OA and OB. Autoradiography showed that between 20 and 50% of the phages from each Petri dish generated a positive signal. It was therefore necessary to purify each of the positive phages by means of a third hybridization cycle. For this purpose, a Pasteur pipette was used to collect those positive lysis plaques which were more isolated from the rest or which were surrounded by lysis plaques that were also positive, and they were resuspended in 1 ml of SM plus 50 μl of chloroform. After diluting this phage solution 100 times and infecting with 15 μl thereof, titres of about 300 lysis plaques per Petri dish were achieved. After processing under identical conditions to the two previous cycles, the result was achieved that 100% of the phages from each Petri dish were positive. In this way 9 independent lysis plaques were purified. Each lysis plaque was resuspended in 100 μl of SM plus 10 μl of chloroform, and with 2 μl of this solution confluent lysis plaques were obtained with the aim of amplifying said positive phages on a solid medium. After collecting the top layer of agarose and resuspending it in 5 ml of SM, solutions with an approximate concentration of $10^7$ pfu/μl were obtained for each of the positive phages.

Using Southern's method (Sambrook et al. (1989) Molecular Cloning: A Laboratory Manual, Cold Spring Harbor Laboratory, Cold Spring Harbor, N.Y., USA), the above-mentioned oligonucleotides OA and OB were also used as a probe to determine the genomic DNA fragments which included the dao gene of *T. variabilis*. For this purpose, hybridization with the DNA digested with the restriction endonucleases (Pharmacia) BamHI, EcoRI, HindIII, KnpI, PstI, PvuII, XbaI and XhoI and fractionated in agarose gel was carried out under the conditions described below. The agarose gel in which DNA fragments were separated on the basis of their molecular size was sequentially incubated at ambient temperature and with gentle agitation for 15 minutes in 0.25 M HCl, 1 hour in denaturing solution and 1 hour in neutralizing solution. The gel was then placed on a wad of Whatman 3 MM filter papers soaked in 10×SSC, and a BA85 nitrocellulose filter (0.45 μm) (Schleicher and Schuell) of the same dimensions as the gel, and soaked in 2×SSC, was placed on it, taking care to avoid the formation of bubbles. Two sheets of Whatman 3MM paper soaked in 2×SSC were placed on the nitrocellulose filter, and 8–10 centimeters in height of dry filter paper of the same dimensions were placed on top, and on top of all this a weight of about 500 grams. The transference process was maintained for 16 hours. Once the DNA had been transferred, the nitrocellulose filter was carefully submerged in 6×SSC for 5 minutes, left to dry for 1 hour at ambient temperature and incubated between two sheets of Whatman 3MM paper at 80° C. with vacuum for 3 hours more in order to fix the DNA to the filter. It was then pre-hybridized and hybridized under the same conditions as described earlier for the screening of the DNA library. The result of the autoradiography showed the appearance of specific hybridization bands for each of the digests. To be precise, the size of these bands was as follows: 10.2 kb for the EcoRI digest, 3.7 kb for the BamHI, 3.5 kb for the HindIII, 11.6 kb for the KpnI, 11.3 for the PstI, 4.8 kb for the PvuII, 2.8 for the XbaI and 4.7 kb for the XhoI.

3. Cloning of the DNA Fragment Which Codes for the dao Gene

After purifying the DNA of the phages as indicated in Section 1 of Example 2 for the bacteriophage λ-GEM12, a SalI digestion was performed, a 9.2 kb band being identified which was subcloned in the plasmid pBluescript I KS(+) (Stratagene) digested with SalI using DNA ligase of the phage T4 (Amersham), ATP and the buffer recommended by the enzyme suppliers. The resultant ligation mixture was incubated for 5 hours at 12° C. and used to transform competent *E. coli* TG1 cells (Amersham). The transformants were selected in a solid LB medium to which ampicillin (100 μg/ml), X-gal (40 μg/ml) and 0.2 mM IPTG had been added. Among the clones which presented the white selection phenotype, the plasmid pALT1 was isolated. Using the Southern technique and the probe OB, the dao gene was then localized in a 3.7 kb BamHI fragment included in the plasmid pALT1. This BamHI fragment was subcloned in the plasmid pBluescript I KS(+) (Stratagene) digested with BamHI. The plasmids pALT2 and pALT3, which contain the 3.7 kb BamHI fragment in both orientations, were thus isolated (FIG. 1).

4. Sequencing of the Fragment Which Contains the dao Gene

The nucleotide sequence of the fragment contained in the plasmid pALT2 was determined on the same plasmid by a previously described method (Sanger et al. (1977) Proc. Natl. Aca. Sci. USA 74, 5463–5464) using the T7 DNA Polymerase Kit (Pharmacia) and [$^{35}$S]dATP. This sequence is shown in SEQ ID NO: 1. Analyses of the sequence and comparison thereof with other sequences known in the international databases (GeneBank/EMBL) indicated that the cloned fragment coded for the dao gene of *T. variabilis*.

EXAMPLE 3

1.—Elimination of the Intron of the dao Gene by PCR

A 0.15-μg DNA sample from the plasmid pALT2 was mixed with 10 μl (25 μM) of each of the following oligonucleotides: DAO1 (5'-CATGCCATGGCTAAAATCGTTGTTATTGGGGCCGG TGTTGCCGGTTTAAC-3') (SEQ ID NO:5) which encodes the complete sequence of the first exon and first nucleotides of the 5' end of the second exon and contained an NcoI restriction site; and DAO2 (5'-CCCAAGCTTCTAAAGGTTTGGACGAG-3') (SEQ ID NO:6) which contained a Hind III restriction site and the sequence of the 3' end corresponding to the second exon of the dao gene, including a translation termination codon. To this mixture were added 2.5 units of Taq polymerase (Perkin-Elmer) together with the appropriate buffer recommended by the suppliers, and the preparation was subjected to an amplification process in a PCR unit (Gene-ATAQ, Pharmacia) using 30 cycles, each cycle being 95° C. (1 minutes), 50° C. (2 minutes) and 72° C. (2.5 minutes). The result of the amplification was visualized by dyeing with ethidium bromide after 1% agarose gel electrophoresis.

The DNA fragment obtained by PCR, of a size of approximately 0.9 kb, was purified by extraction of the agarose gel using β-agarase (Biolabs), in accordance with the manufacturer's recommendations. 0.2 μg of the purified fragment was ligated with 1 μg of the vector M13tg130 (Amersham) digested with the enzyme HincII (Pharmacia) by means of the DNA ligase of the phage T4 (Amersham), in the presence of ATP, using the buffer recommended by the supplier. In this way the phage M13DAO was produced (FIG. 1), which was then sequenced in order to check that the intron had been adequately eliminated. The nucleotide sequence of the fragment contained in phage M13DAO was determined on the same recombinant phage by a previously described method (Sanger et al. (1977) Proc. Natl. Aca. Sci. USA 74:5463–5464) using the T7 DNA Polymerase Kit (Pharmacia) and [$^{35}$S]dATP. The nucleotide sequence revealed that the cloned fragment had 0.9 kb and contained the sequence of the dao gene of *T. variabilis* without the intron.

2.—Subcloning of the dao Gene Without any Intron in pKK233.2

A 0.1-μg DNA sample from the plasmid pKK233.2 was digested with the restriction endonucleases NcoI and HindIII (Pharmacia) at 37° C., in a buffer recommended by the suppliers, for 1 hour, and was heated for 10 minutes at 65° C. in order to stop the reaction. The digested plasmid was mixed with 0.2 μg of the phage M13DAO digested with the same restriction endonucleases indicated above, and both DNAs were ligated by means of the enzyme DNA ligase of the phage T4 (Amersham), in the presence of ATP, using the buffer recommended by the supplier.

The resultant ligation mixture was used to transform competent *E. coli* TG1 cells. The transformants were isolated in LB medium with ampicillin (100 μg/ml). By this procedure a clone was obtained which contained the recombinant plasmid pKDAO3 (FIG. 1) which has the 0.9-kb DNA fragment resulting from the amplification by PCR inserted between the NcoI and HindIII sites of the plasmid pKK233.2, i.e. expressed under the control of the trc promoter.

EXAMPLE 4

1.—Design of a Chimeric DAO Enzyme Containing a Tail of 6 Histidines

In order to insert the polyhistidine tail at the amino terminal end of the DAO enzyme of *T. variabilis*, 0.1 μg of the plasmid pKDAO3 was digested with the restriction endonuclease NcoI (Pharmacia) for 1 hour at 37° C., under the conditions recommended by the supplier, and it was heated for 10 minutes at 65° C. to stop the reaction. The plasmid so digested was treated with the Klenow fragment of the DNA polymerase I of *E. coli* (Pharmacia), in accordance with the instructions recommended by the supplier, and the sample was then heated for 10 minutes at 65° C. to stop the reaction. The resultant linearized plasmid was ligated to a DNA fragment which contains the nucleotide sequence coding for 6 histidine residues, by means of the enzyme DNA ligase of the phage T4 (Amersham) in the presence of ATP, using the buffer recommended by the supplier. The coding fragment of the 6 histidine residues was obtained by means of a mixture of 1.5 μg of two complementary oligonucleotides, called HIS1 (5'-CATCATCACCACCATCACTT-3') and HIS2 (5'-AAGTGATGGTGGTGATGATG-3'), which were subsequently heated to 100° C. for 5 minutes and cooled to ambient temperature to hybridize, forming a double-stranded DNA fragment.

The resultant ligation mixture was used to transform competent *E. coli* TG1 cells. The transformants were isolated in LB medium with ampicillin (100 μg/ml). By this procedure a clone was obtained which contained the recombinant plasmid pKDAOHIS which has the dao gene linked to a sequence of 18 nucleotides which code for 6 histidine residues at the 5' end. In order to check that the plasmid pKDAOHIS (FIG. 1) contained the expected chimeric construct, the sequence was determined on the same recombinant plasmid by a previously described method (Sanger et al. (1977) Proc. Natl. Aca. Sci. USA 74: 5463–5464) using the T7 DNA Polymerase Kit (Pharmacia) and [$^{35}$S]dATP. The sequence obtained is shown in SEQ ID NO: 2.

The strain *E. coli* TG1 transformed with the plasmid pKDAOHIS was fermented in the LB medium for 20 hours at 25° C. and 250 rpm. The cells were then collected by centrifugation at 5000×g for 10 minutes and disrupted by sonication, and their DAO activity was assayed as described in Section 1 of Example 1. The DAO activity obtained by this procedure was 350 U/mg of protein. In this way it was confirmed that the chimeric DAO enzyme with the histidines chain (hisDAO) so obtained was active. Furthermore, using SDS-polyacrylamide gel electrophoresis, it was confirmed that, as was to be expected, the enzyme hisDAO had a slightly greater size than the native DAO enzyme. The strain *E. coli* TG1 transformed with the plasmid pKDAOHIS was deposited in the Spanish Type Culture Collection (CECT), located at the Department of Microbiology in the Faculty of Biological Sciences, University of Valencia, 46100 Burjasot (Valencia), on 10.06.97, with the deposit number CECT4888.

EXAMPLE 5

1.—Preparation of the Agarose-metal Chelate Support

A mixture of 5.7 ml of epichlorohydrin and 11.4 ml of ethylene glycol dimethyl ether is slowly added to a suspension of 7 g of agarose CL6B in 57 ml of a 0.1 N NaOH solution containing 340 mg of NaBH$_4$, and the suspension is gently stirred continuously for 4 hours at 25° C. The agarose-epoxide so obtained is washed with ample distilled water and added to a solution made up of 2.5 ml of 2 M sodium iminodiacetate and 19 ml of 0.1 M sodium bicarbonate buffer, pH 11. This suspension is gently stirred continuously for 12 hours at 25° C. Finally the support is washed with distilled water and resuspended in an aqueous solution which contains the metal salt desired (5 mg/ml). The agarose-metal chelate support thus formed is washed with ample water and prepared for subsequent use. When CoCl$_2$ is added as the metal salt, an agarose-cobalt chelate support is obtained.

2.—Purification of the Chimeric hisDAO Enzyme on the Agarose-cobalt Chelate Support The column containing the agarose-cobalt chelate support is equilibrated with 20 mM sodium phosphate buffer (pH 7.0) and 0.2 M NaCl. The soluble cell extract obtained as described in the preceding example from E. coli TG1 cells transformed with the plasmid pKDAOHIS is loaded on this column. When the extract has been loaded, the column is washed with ample amounts of the same equilibration buffer, thus eliminating all the proteins of the extract except hisDAO, which remains retained in the column. The enzyme hisDAO is then eluted using a 20 mM sodium phosphate buffer, pH 7.0, which contains 10 mM imidazole. The fractions which contain the enzyme hisDAO are collected and dialysed against 20 mM sodium phosphate buffer, pH 7.0. The enzyme (9000 U/mg) thus prepared exhibits a degree of purity higher than 90% and is ready to be used for the transformation of cephalosporin C into GL-7ACA.

DETAILED DESCRIPTION OF THE FIGURES

FIG. 1.—Process for Construction of the Plasmid pKDAO-HIS

The dao gene, lacking any intron and with an NcoI site in the ATG which codes for the first methionine of the protein, was obtained by PCR from the plasmid pALT2. The fragment amplified by PCR was then subcloned at the HincII site of the vector M13tg130, giving M13DAO. An NcoI-HindIII fragment obtained from M13DAO was subcloned at the NcoI-HindIII sites of the plasmid pKK233.2, giving rise to pKDAO3. This plasmid has the dao gene expressed under the control of the trc promoter of E. coli. Finally, the DNA fragment coding for the polyhistidines tail at the 5' end of the dao gene was introduced, producing the plasmid pKDAO-HIS.

What is claimed is:

1. A process for producing enzymatically active modified *Trigonopsis variabilis* D-aminoacid oxidase enzyme in a bacterial host organism, characterized by the following operations:

(a) isolating the DNA of the gene which codes for the D-aminoacid oxidase activity of *Trigonopsis variabilis*, wherein said gene contains an intron;

(b) eliminating the intron which is contained in said gene by means of a procedure based on the use of synthetic oligonucleotides and the polymerase chain reaction (PCR) to obtain a DNA fragment;

(c) inserting the DNA fragment obtained in (b) into a plasmid which is able to replicate in the host organism;

(d) fusing, at the 5' end of the structural region of the gene lacking any intron which codes for D-aminoacid oxidase activity, a synthetic fragment which contains a nucleotide sequence coding for six histidines;

(e) transforming the host organism with the recombinant plasmid resulting from (d);

(f) growing the transformed cells of the host organism obtained in (e) in a suitable culture medium under conditions that allow the production of enzymatically active D-aminoacid oxidase; and (g) recovering the enzyme D-aminoacid oxidase from the culture of operation (f) by means of cobalt chelate affinity chromatography.

2. A process according to claim 1, wherein the host organism is *Escherichia coli*.

3. A process according to claim 1, wherein the affinity chromatography utilizes a support based on divalent cations.

4. The D-amino acid oxidase enzyme modified and purified by the process of claim 3.

5. A process for the enzymatic synthesis of 7β-(4-carboxybutanamide) cephalosporanic acid comprising reacting cephalosporin C with a fusion protein comprising polyhistidine and the enzyme D-aminoacid oxidase obtained by the process according to claim 1.

6. A process according to claim 5, characterized by reacting cephalosporin C with the fusion protein in an aqueous medium.

* * * * *

UNITED STATES PATENT AND TRADEMARK OFFICE
CERTIFICATE OF CORRECTION

PATENT NO. : 6,635,458 B2
DATED : October 21, 2003
INVENTOR(S) : Garcia Lopez et al.

It is certified that error appears in the above-identified patent and that said Letters Patent is hereby corrected as shown below:

Title page, Item [54] and Column 1, line 4,
Title, "7$B(G)" should read -- 7β --

Title page,
Item [56], References Cited, OTHER PUBLICATIONS, "Schrader and Andreesen (sic) Jr." reference, "Andreeses" should read -- Andressen --; "important" should read -- importance --; and "*viriabilis*" should read -- *variabilis* --
"Schrader and Andreesen Jr." reference, "*viriabilis*" should read -- *variabilis* --;
"Alonso et al.," reference, "*viriabilis*" should read -- *variabilis* --
"Hochuli", reference, "Chromatoraphy" should read -- Chromatography --;
"Pollegioni et al.," reference, "Internatonal" should read -- International --; and
"Derwent", reference, "if" should read -- of --

Item [57], ABSTRACT,
Line 6, "to gene" should read -- to the gene --
Lines 8 and 13, "plasmide" should read -- plasmid --

Item [73], Assignee, "Leon (ES)" should read -- León (ES) --
Item [75], Inventors, "Cortes" should read -- Cortés --; and
"Franciso" should read -- Francisco --;
"Jose" (first occurrence) should read -- José --; "Jose" (second and third occurrences) should read -- Josè --; "Encarnacion" should read -- Encarnación --; and
"Leon (ES)" (three occurrences) should read -- León (ES) --

Column 2,
Line 1, "tred" should read -- tered --

Column 4,
Line 24, "Co2+-IDA" should read -- $Co^{2+}$-IDA --

Column 5,
Line 15, "Cola" should read -- Cold --
Lines 49 and 54, "analysed" should read -- analyzed --

UNITED STATES PATENT AND TRADEMARK OFFICE
CERTIFICATE OF CORRECTION

PATENT NO.    : 6,635,458 B2
DATED         : October 21, 2003
INVENTOR(S)   : Garcia Lopez et al.

It is certified that error appears in the above-identified patent and that said Letters Patent is hereby corrected as shown below:

Column 6,
Line 23, "Rg" should read -- µg --
Line 31, "analysed" should read -- analyzed --
Line 39, "analysing" should read -- analyzing --
Line 48, "0.25 ,µg" should read -- 0.25 µg --

Column 7,
Line 54, "titres" should read -- titers --

Signed and Sealed this

Second Day of March, 2004

JON W. DUDAS
*Acting Director of the United States Patent and Trademark Office*

SEQUENCE LISTING

<160> NUMBER OF SEQ ID NOS: 6

<210> SEQ ID NO 1
<211> LENGTH: 3668
<212> TYPE: DNA
<213> ORGANISM: Trigonosis variabilis
<220> FEATURE:
<221> NAME/KEY: CDS
<222> LOCATION: (1481)...(1503)
<223> OTHER INFORMATION: dao gene
<220> FEATURE:
<221> NAME/KEY: CDS
<222> LOCATION: (1543)...(2586)
<223> OTHER INFORMATION: dao gene
<220> FEATURE:
<221> NAME/KEY: intron
<222> LOCATION: (1504)...(1542)
<220> FEATURE:
<221> NAME/KEY: CDS
<222> LOCATION: (2952)...(3668)
<223> OTHER INFORMATION: ORF1

<400> SEQUENCE: 1

```
ggatccttac gaggaagatc tgataatgga gaattctctc gctttatgcc atgacttgca      60
ggttcctcgg gtaatggaac cactgacaaa tcggctgctt gaggttttgt tcccttcaac     120
acttcatctt ccaaggttct aattcgtagt ttcttctcat tcaataaagc tgcaaaccgc     180
tccaacattt gtagatcatt attctttgtc ttcacggcaa ctgtatctag ttccttctga     240
aggtccttcg tttctttggt tagtagatct accatgccag ttaagcgatc aatctcctct     300
tggacctcct tcttgagcga tagctctgac cagaaccaat caaaagaac  accaggatcg     360 gtacatgttc cttgtcggga tagggacagt gatcccaaag taattgatag atcctgaact     420
ttctgggtaa tcgagataat aaccgaactc aaatcttgtg atggcttggc gttcaattga     480
atgttttcgc tagaaagcct cggactctta cgttggtctt catctgtaag cgaccgcgtg     540
aacagttgtt ggaataagtc attccattca ctttcacttt gaggacttct atttgaccgt     600
agatctttaa ttgactcatt tccagttact gaaagttagc tggaagcttt caacatgtcc     660
tcaccagagg tttgatagag gtctaacgat ggcttcatac aggctgtgaa tgtgattgtt     720
tcgccagtct caactctgac gatcaaacgc ttagatccac caatctcaat accgaacgag     780
```

```
                                                                -continued ttaattcgac tcattgctca atatgattga tcgcgcggga tgacatcgaa ggtgacaacc      840
gtacgcgaaa gatgcgtgac gataaggaca cgactaagg gagtagatgg actggggagt       900
gaaggaaatg tgagactaga gaaaagccac tgactgagag taaaacagcc atgattagac      960
aatcagccat gacagcacta taacgtgata tgataagtaa ggctctgttg cccgctgacg     1020
gccaacggct gacggccaac ttgatgattc taccacaaaa aatcatacga aagtcaacg     1080 aaaagtcctt agtttggaat tccagacatg gcagaattta acggccacta cagttggccg    1140
ttcgtaaacg agacaagtga ctcatggcag caccgtctca gtccaccggt ctaaagcact    1200
tggtgccaga tgaatttgga aactgtcacc ttatagaatt acttttggat agttttgta    1260 aggctggaga cttgtaagcc tgactcagtt gactcatcgg cgaaagcttc ctatcttgga   1320
gctaagatcg cctgatcgtt ttgccctact tatcttggtt gcatgagttg ccggtcaga   1380 gccgcattct agccaaaggg ttatagcgtt acactcttga taggcaaatc cgtgctcgga  1440
ttatatataa ggcaaaagtc gattcaacgg atcaataaaa atg gct aaa atc gtt   1495
                                                Met Ala Lys Ile Val
                                                  1               5 gtt att gg gtaagtgcct tgataccaga cggctgacat ttgtttag t gcc ggt    1548
Val Ile Gly                                                Ala Gly
                                                              10 gtt gcc ggt tta act aca gct ctt caa ctt ctt cgt aaa gga cat gag   1596
Val Ala Gly Leu Thr Thr Ala Leu Gln Leu Leu Arg Lys Gly His Glu
            15                  20                  25 gtt aca att gtg tcc gag ttt acg ccc ggt gat ctt agt atc gga tat   1644
Val Thr Ile Val Ser Glu Phe Thr Pro Gly Asp Leu Ser Ile Gly Tyr
        30                  35                  40 acc tcg cct tgg gca ggt gcc aac tgg ctc aca ttt tac gat gga ggc   1692
Thr Ser Pro Trp Ala Gly Ala Asn Trp Leu Thr Phe Tyr Asp Gly Gly
    45                  50                  55 aag tta gcc gac tac gat gcc gtc tct tat cct atc ttg cga gag ctg   1740
Lys Leu Ala Asp Tyr Asp Ala Val Ser Tyr Pro Ile Leu Arg Glu Leu
60                  65                  70 gct cga agc agc ccc gag gct gga att cga ctc atc aac caa cgc tcc   1788
Ala Arg Ser Ser Pro Glu Ala Gly Ile Arg Leu Ile Asn Gln Arg Ser
75                  80                  85                  90 cat gtt ctc aag cgt gat ctt cct aaa ctg gaa ggt gcc atg tcg gcc   1836
His Val Leu Lys Arg Asp Leu Pro Lys Leu Glu Gly Ala Met Ser Ala
                95                 100                 105 atc tgt caa cgc aac ccc tgg ttc aaa aac aca gtc gat tct ttc gag   1884
Ile Cys Gln Arg Asn Pro Trp Phe Lys Asn Thr Val Asp Ser Phe Glu
            110                 115                 120 att atc gag gac agg tcc agg att gtc cac gat gat gtg gct tat cta   1932
Ile Ile Glu Asp Arg Ser Arg Ile Val His Asp Asp Val Ala Tyr Leu
        125                 130                 135 gtc gaa ttt gct tcc gtt tgt atc cac acc gga gtc tac ttg aac tgg   1980
Val Glu Phe Ala Ser Val Cys Ile His Thr Gly Val Tyr Leu Asn Trp
    140                 145                 150 ctg atg tcc caa tgc tta tcg ctc ggc gcc acg gtg gtt aaa cgt cga   2028
Leu Met Ser Gln Cys Leu Ser Leu Gly Ala Thr Val Val Lys Arg Arg
155                 160                 165                 170 gtg aac cat atc aag gat gcc aat tta cta cac tcc tca gga tca cgc   2076
Val Asn His Ile Lys Asp Ala Asn Leu Leu His Ser Ser Gly Ser Arg
                175                 180                 185 ccc gac gtg att gtc aac tgt agt ggt ctc ttt gcc cgg ttc ttg gga   2124
Pro Asp Val Ile Val Asn Cys Ser Gly Leu Phe Ala Arg Phe Leu Gly
            190                 195                 200
```

```
ggc gtc gag gac aag aag atg tac cct att cga gga caa gtc gtc ctt          2172
Gly Val Glu Asp Lys Lys Met Tyr Pro Ile Arg Gly Gln Val Val Leu
        205                 210                 215 gtt cga aac tct ctt cct ttt atg gcc tcc ttt tcc agc act cct gaa          2220
Val Arg Asn Ser Leu Pro Phe Met Ala Ser Phe Ser Ser Thr Pro Glu
        220                 225                 230 aaa gaa aat gaa gac gaa gct cta tat atc atg acc cga ttc gat ggt          2268
Lys Glu Asn Glu Asp Glu Ala Leu Tyr Ile Met Thr Arg Phe Asp Gly
235                 240                 245                 250 act tct atc att ggc ggt tgt ttc caa ccc aac aac tgg tca tcc gaa          2316
Thr Ser Ile Ile Gly Gly Cys Phe Gln Pro Asn Asn Trp Ser Ser Glu
                255                 260                 265 ccc gat cct tct ctc acc cat cga atc ctg tct aga gcc ctc gac cga          2364
Pro Asp Pro Ser Leu Thr His Arg Ile Leu Ser Arg Ala Leu Asp Arg
        270                 275                 280 ttc ccg gaa ctg acc aaa gat ggc cct ctt gac att gtg cgc gaa tgc          2412
Phe Pro Glu Leu Thr Lys Asp Gly Pro Leu Asp Ile Val Arg Glu Cys
        285                 290                 295 gtt ggc cac cgt cct ggt aga gag ggc ggt ccc cga gta gaa tta gag          2460
Val Gly His Arg Pro Gly Arg Glu Gly Gly Pro Arg Val Glu Leu Glu
300                 305                 310 aag atc ccc ggc gtt ggc ttt gtt gtc cat aac tat ggt gcc gcc ggt          2508
Lys Ile Pro Gly Val Gly Phe Val Val His Asn Tyr Gly Ala Ala Gly
315                 320                 325                 330 gct ggt tac cag tcc tct tac ggc atg gct gat gaa gct gtt tct tac          2556
Ala Gly Tyr Gln Ser Ser Tyr Gly Met Ala Asp Glu Ala Val Ser Tyr
                335                 340                 345 gtc gaa aga gct ctt act cgt cca aac ctt tagaaatcat gtatacaatt           2606
Val Glu Arg Ala Leu Thr Arg Pro Asn Leu
        350                 355 attctctctc tataaatcta attttttttgt gtggtctaat attcgtaaac acgtcgcagt       2666
cgtctatgtc gccctcgtca ccgtgtccaa agtcgtaaag tgactgattg caattgcgac        2726
aacacgtgac tcgacctgcc tccttacctc ccatcaacaa caaaagaagc tggctaagat        2786
agaggtctgt tgacgagcac tcgtaagaac ggcaaacata gaaaggaggc tctataatta       2846
cctggaaact gtgttatata ctatcactag tgagggtgag tgattagaag caaggggact       2906
agaatactga catggataga gatccaggag cctataaaat aatca atg aat aca att       2963
                                                Met Asn Thr Ile
                                                        360 gat ttg gaa tct tgg gat gat gat cca gat ttc gca gat gac ttt gag          3011
Asp Leu Glu Ser Trp Asp Asp Asp Pro Asp Phe Ala Asp Asp Phe Glu
                365                 370                 375 aat tta aag act cca gct cct acg ttt tat gaa gcc aac gat gag att          3059
Asn Leu Lys Thr Pro Ala Pro Thr Phe Tyr Glu Ala Asn Asp Glu Ile
        380                 385                 390 agg gat gga gaa gaa gag gat gat ttt ttc tct caa gat ttc gag ttg          3107
Arg Asp Gly Glu Glu Glu Asp Asp Phe Phe Ser Gln Asp Phe Glu Leu
        395                 400                 405 gat gat aag aat aca ctc gga cga cag aac aag att tcg act agt cac          3155
Asp Asp Lys Asn Thr Leu Gly Arg Gln Asn Lys Ile Ser Thr Ser His
        410                 415                 420 cta aag tcc gcg agt cag gaa caa gca gag acc tcc ttt cgt gac tcg          3203
Leu Lys Ser Ala Ser Gln Glu Gln Ala Glu Thr Ser Phe Arg Asp Ser
425                 430                 435                 440 aac gct ggc gtc aat gct ttc agc tgc ggg act ata aaa gcc tta gga          3251
Asn Ala Gly Val Asn Ala Phe Ser Cys Gly Thr Ile Lys Ala Leu Gly
                445                 450                 455
```

```
aag aat agg atg acg acg gtg gaa gag aag tgg gaa aag gaa gtt aga    3299
Lys Asn Arg Met Thr Thr Val Glu Glu Lys Trp Glu Lys Glu Val Arg
        460                 465                 470 cgc gat caa att ggg ttc aat gaa gct act ctt aga gct cat gag act    3347
Arg Asp Gln Ile Gly Phe Asn Glu Ala Thr Leu Arg Ala His Glu Thr
        475                 480                 485 acc aga gaa tgg tta aaa tcc cag act ggc gaa gct ggg act aaa agc    3395
Thr Arg Glu Trp Leu Lys Ser Gln Thr Gly Glu Ala Gly Thr Lys Ser
        490                 495                 500 aag gtc ttt agc cca att ctc gac gga tca ttc ttc gaa ccg cct ttg    3443
Lys Val Phe Ser Pro Ile Leu Asp Gly Ser Phe Phe Glu Pro Pro Leu
505                 510                 515                 520 gaa tct aaa gtc agg cgt tat cat tca ccc cgg aaa cag gca cct cct    3491
Glu Ser Lys Val Arg Arg Tyr His Ser Pro Arg Lys Gln Ala Pro Pro
                525                 530                 535 cct cct cct gac gat ttt tca gat gca ttt gaa cta tct aca gaa gag    3539
Pro Pro Pro Asp Asp Phe Ser Asp Ala Phe Glu Leu Ser Thr Glu Glu
        540                 545                 550 cca ctg aaa tta aaa gtc caa cca gtt caa cct cat atg acg cct gct    3587
Pro Leu Lys Leu Lys Val Gln Pro Val Gln Pro His Met Thr Pro Ala
        555                 560                 565 ctg agt gat aat gat cta tgg ggt gag gaa tct att ggt gtg cga cga    3635
Leu Ser Asp Asn Asp Leu Trp Gly Glu Glu Ser Ile Gly Val Arg Arg
        570                 575                 580 gga ggc agg gac tcg tca agt atg gga gga tcc                        3668
Gly Gly Arg Asp Ser Ser Ser Met Gly Gly Ser
585                 590                 595

<210> SEQ ID NO 2
<211> LENGTH: 1128
<212> TYPE: DNA
<213> ORGANISM: Trigonosis variabilis
<220> FEATURE:
<221> NAME/KEY: CDS
<222> LOCATION: (16)...(1107)
<223> OTHER INFORMATION: dao gene with an addition in 5' of a nucleotide
      coding for a polyhistidine of 6 (his DAO)

<400> SEQUENCE: 2
cacaggaaac agacc atg cat cat cac cac cat cac ttc atg gct aaa atc     51
              Met His His His His His His Phe Met Ala Lys Ile
              1               5                   10 gtt gtt att ggg gcc ggt gtt gcc ggt tta act aca gct ctt caa ctt     99
Val Val Ile Gly Ala Gly Val Ala Gly Leu Thr Thr Ala Leu Gln Leu
        15                  20                  25 ctt cgt aaa gga cat gag gtt aca att gtg tcc gag ttt acg ccc ggt    147
Leu Arg Lys Gly His Glu Val Thr Ile Val Ser Glu Phe Thr Pro Gly
    30                  35                  40 gat ctt agt atc gga tat acc tcg cct tgg gca ggt gcc aac tgg ctc    195
Asp Leu Ser Ile Gly Tyr Thr Ser Pro Trp Ala Gly Ala Asn Trp Leu
45                  50                  55                  60 aca ttt tac gat gga ggc aag tta gcc gac tac gat gcc gtc tct tat    243
Thr Phe Tyr Asp Gly Gly Lys Leu Ala Asp Tyr Asp Ala Val Ser Tyr
                65                  70                  75 cct atc ttg cga gag ctg gct cga agc agc ccc gag gct gga att cga    291
Pro Ile Leu Arg Glu Leu Ala Arg Ser Ser Pro Glu Ala Gly Ile Arg
            80                  85                  90 ctc atc aac caa cgc tcc cat gtt ctc aag cgt gat ctt cct aaa ctg    339
Leu Ile Asn Gln Arg Ser His Val Leu Lys Arg Asp Leu Pro Lys Leu
        95                  100                 105 gaa ggt gcc atg tcg gcc atc tgt caa cgc aac ccc tgg ttc aaa aac    387
Glu Gly Ala Met Ser Ala Ile Cys Gln Arg Asn Pro Trp Phe Lys Asn
```

```
aca gtc gat tct ttc gag att atc gag gac agg tcc agg att gtc cac      435
Thr Val Asp Ser Phe Glu Ile Ile Glu Asp Arg Ser Arg Ile Val His
125             130                 135                 140 gat gat gtg gct tat cta gtc gaa ttt gct tcc gtt tgt atc cac acc      483
Asp Asp Val Ala Tyr Leu Val Glu Phe Ala Ser Val Cys Ile His Thr
                145                 150                 155 gga gtc tac ttg aac tgg ctg atg tcc caa tgc tta tcg ctc ggc gcc      531
Gly Val Tyr Leu Asn Trp Leu Met Ser Gln Cys Leu Ser Leu Gly Ala
                160                 165                 170 acg gtg gtt aaa cgt cga gtg aac cat atc aag gat gcc aat tta cta      579
Thr Val Val Lys Arg Arg Val Asn His Ile Lys Asp Ala Asn Leu Leu
            175                 180                 185 cac tcc tca gga tca cgc ccc gac gtg att gtc aac tgt agt ggt ctc      627
His Ser Ser Gly Ser Arg Pro Asp Val Ile Val Asn Cys Ser Gly Leu
        190                 195                 200 ttt gcc cgg ttc ttg gga ggc gtc gag gac aag aag atg tac cct att      675
Phe Ala Arg Phe Leu Gly Gly Val Glu Asp Lys Lys Met Tyr Pro Ile
205                 210                 215                 220 cga gga caa gtc gtc ctt gtt cga aac tct ctt cct ttt atg gcc tcc      723
Arg Gly Gln Val Val Leu Val Arg Asn Ser Leu Pro Phe Met Ala Ser
                225                 230                 235 ttt tcc agc act cct gaa aaa gaa aat gaa gac gaa gct cta tat atc      771
Phe Ser Ser Thr Pro Glu Lys Glu Asn Glu Asp Glu Ala Leu Tyr Ile
            240                 245                 250 atg acc cga ttc gat ggt act tct atc att ggc ggt tgt ttc caa ccc      819
Met Thr Arg Phe Asp Gly Thr Ser Ile Ile Gly Gly Cys Phe Gln Pro
        255                 260                 265 aac aac tgg tca tcc gaa ccc gat cct tct ctc acc cat cga atc ctg      867
Asn Asn Trp Ser Ser Glu Pro Asp Pro Ser Leu Thr His Arg Ile Leu
270                 275                 280 tct aga gcc ctc gac cga ttc ccg gaa ctg acc aaa gat ggc cct ctt      915
Ser Arg Ala Leu Asp Arg Phe Pro Glu Leu Thr Lys Asp Gly Pro Leu
285                 290                 295                 300 gac att gtg cgc gaa tgc gtt ggc cac cgt cct ggt aga gag ggc ggt      963
Asp Ile Val Arg Glu Cys Val Gly His Arg Pro Gly Arg Glu Gly Gly
                305                 310                 315 ccc cga gta gaa tta gag aag atc ccc ggc gtt ggc ttt gtt gtc cat     1011
Pro Arg Val Glu Leu Glu Lys Ile Pro Gly Val Gly Phe Val Val His
            320                 325                 330 aac tat ggt gcc gcc ggt gct ggt tac cag tcc tct tac ggc atg gct     1059
Asn Tyr Gly Ala Ala Gly Ala Gly Tyr Gln Ser Ser Tyr Gly Met Ala
        335                 340                 345 gat gaa gct gtt tct tac gtc gaa aga gct ctt act cgt cca aac ctt     1107
Asp Glu Ala Val Ser Tyr Val Glu Arg Ala Leu Thr Arg Pro Asn Leu
350                 355                 360 tagaagcttg gctgttttgg c                                              1128
```

<210> SEQ ID NO 3
<211> LENGTH: 16
<212> TYPE: DNA
<213> ORGANISM: Trigonosis variabilis
<220> FEATURE:
<223> OTHER INFORMATION: Oligonucleotide OA

<400> SEQUENCE: 3
tcttgtcctc gacacc                                                      16

<210> SEQ ID NO 4
<211> LENGTH: 18

```
<212> TYPE: DNA
<213> ORGANISM: Trigonosis variabilis
<220> FEATURE:
<223> OTHER INFORMATION: Oligonucleotide OB

<400> SEQUENCE: 4
gacgtggatt gtcaactg                                                 18

<210> SEQ ID NO 5
<211> LENGTH: 50
<212> TYPE: DNA
<213> ORGANISM: Trigonosis variabilis
<220> FEATURE:
<223> OTHER INFORMATION: Oligonucleotide primer

<400> SEQUENCE: 5
catgccatgg ctaaaatcgt tgttattggg gccggtgttg ccggtttaac               50

<210> SEQ ID NO 6
<211> LENGTH: 26
<212> TYPE: DNA
<213> ORGANISM: Trigonosis variabilis
<220> FEATURE:
<223> OTHER INFORMATION: Oligonucleotide primer

<400> SEQUENCE: 6
cccaagcttc taaaggtttg gacgag                                        26
```